United States Patent
Matsubara et al.

(10) Patent No.: US 8,496,577 B2
(45) Date of Patent: Jul. 30, 2013

(54) ENDOSCOPE APPARATUS, METHOD, AND COMPUTER READABLE MEDIUM

(75) Inventors: Kenta Matsubara, Kanagawa (JP); Hiroshi Yamaguchi, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 284 days.

(21) Appl. No.: 13/088,973

(22) Filed: Apr. 18, 2011

(65) Prior Publication Data

US 2012/0265014 A1 Oct. 18, 2012

(30) Foreign Application Priority Data

Apr. 19, 2010 (JP) .................................. 2010-096279

(51) Int. Cl.
*A61B 1/04* (2006.01)
*A61B 1/00* (2006.01)
*A61B 5/00* (2006.01)
*G01J 3/30* (2006.01)
*H04N 7/18* (2006.01)

(52) U.S. Cl.
USPC ........... 600/118; 600/109; 600/310; 356/317; 348/155

(58) Field of Classification Search
USPC ......................................... 128/922; 348/155
See application file for complete search history.

(56) References Cited

U.S. PATENT DOCUMENTS

| 4,273,959 A * | 6/1981 | Tuda et al. ..................... 704/276 |
| 6,734,893 B1 * | 5/2004 | Hess et al. ...................... 348/68 |
| 2009/0281390 A1 * | 11/2009 | Qiu et al. ..................... 600/199 |
| 2010/0063352 A1 * | 3/2010 | Matsuura ..................... 600/103 |
| 2011/0054336 A1 * | 3/2011 | Jornod .......................... 600/509 |

FOREIGN PATENT DOCUMENTS

| JP | 2008-93220 A | 4/2008 |
| JP | 2008-188165 A | 8/2008 |
| JP | 2009-236846 A | 10/2009 |

* cited by examiner

*Primary Examiner* — John P Leubecker
*Assistant Examiner* — Ronald D Colque
(74) *Attorney, Agent, or Firm* — Birch, Stewart, Kolasch & Birch, LLP (57) ABSTRACT

An endoscope apparatus comprising an irradiating section that switches over time between irradiating a target with light in a first wavelength region and light in a second wavelength region; a light receiving section that receives returned light from the target; a movement identifying section that identifies movement of the target, based on an image of the target captured using returned light from the target irradiated by light in the first wavelength region; a control section that that predicts timings at which a phase of the movement of the target is a predetermined phase, based on the movement identified by the movement identifying section, and causes the irradiating section to emit light in the second wavelength region at the predicted timings; and an image generating section that generates an image of the target based on the returned light received by the light receiving section at the predicted timings.

15 Claims, 7 Drawing Sheets

| DISPLACEMENT AMOUNT | DEFORMATION AMOUNT | EXPOSURE TIME |
|---|---|---|
| ○○ | △△ | ×× |
| ⋮ | ⋮ | ⋮ |

ENDOSCOPE APPARATUS, METHOD, AND COMPUTER READABLE MEDIUM

BACKGROUND

1. Technical Field

The present invention relates to an endoscope apparatus, a method, and a computer readable medium. The contents of the following Japanese patent application are incorporated herein by reference, NO. 2010-096279 filed on Apr. 19, 2010.

2. Related Art

A technique is known for obtaining a fluorescent image via multiple exposure each time respiration or pulse of an organism enters a prescribed state, as shown in Patent Document 1, for example. Another technique is known for capturing an image of a heart only in a diastolic state, based on the waveform of an electrocardiogram, to obtain a detailed still image without blur, as shown in Patent Document 2, for example. Yet another technique is known for capturing a plurality of radiographic images at timings when identical pulse phases are detected from a subject and superimposing these radiographic images on each other, as shown in Patent Document 3, for example.

Patent Document 1: Japanese Patent Application Publication No. 2009-236846
Patent Document 2: Japanese Patent Application Publication No. 2008-93220
Patent Document 3: Japanese Patent Application Publication No. 2008-188165

When capturing an image of a target under observation using weak light with a low intensity, as in fluorescent observation, it is necessary to expose the target to light for a long time due the increased signal-to-noise ratio. If the target moves during the long exposure time, the fluorescent image becomes blurred. Movement of the target is not limited to the pulse-like motion of respiration or a heart beat, and may also include a combination of a variety of movements such as the peristaltic movement of intestines. In this case, image blue occurs when image capturing is performed based on a cardiographic signal or respiration signal. Therefore, there is a problem that weak light images with little blur and high signal-to-noise ratios cannot be obtained.

SUMMARY

In order to solve the above problems, according to a first aspect related to the innovations herein, provided is an endoscope apparatus comprising an irradiating section that switches over time between irradiating a target with light in a first wavelength region and light in a second wavelength region; a light receiving section that receives returned light from the target irradiated with the light from the irradiating section; a movement identifying section that identifies movement of the target, based on a first image of the target captured as a result of the light receiving section receiving first returned light, which is returned light from the target irradiated by the light in the first wavelength region; a timing predicting section that predicts a plurality of timings at which a phase of the movement of the target is a predetermined phase, based on the movement identified by the movement identifying section; a control section that causes the irradiating section to emit the light in the second wavelength region at the timings predicted by the timing predicting section and causes the light receiving section to receive second returned light, which is returned light from the target irradiated by the light in the second wavelength region; and an image generating section that generates a second image of the target based on the second returned light received by the light receiving section at the timings predicted by the timing predicting section.

The control section may cause the light receiving section to receive the first returned light at one or more timings between temporally adjacent timings among the timings predicted by the timing predicting section, and the image generating section may generate the first image at each of the one or more timings, based on the first returned light received by the light receiving section.

The control section may cause the light receiving section to receive the second returned light at each of the timings predicted by the timing predicting section, over a period longer than the period during which the light receiving section receives the first returned light to capture one of the first images.

The endoscope apparatus may further comprise a light receiving time setting section that sets length of a light receiving period during which the light receiving section receives the second returned light at the timings predicted by the timing predicting section, based on the movement identified by the movement identifying section, and the control section may cause the light receiving section to receive the second returned light for the period length set by the light receiving time setting section.

The light receiving time setting section may identify movement amount of the target at the timings predicted by the timing predicting section, based on the movement identified by the movement identifying section, and set the light receiving period to be longer when the identified movement amount is larger.

The light in the second wavelength region may be excitation light that excites a luminescent substance in the target, and the second returned light is luminescent light generated by the luminescent substance being excited by the excitation light.

The light in the second wavelength region may be light in a narrower band than the light in the first wavelength region.

The light in the first wavelength region may be light in a visible wavelength region.

The image generating section may generate the second image by adding together signals indicating an amount of the second returned light received by the light receiving section at each of the timings predicted by the timing predicting section.

The control section may cause light receiving elements of the light receiving section to receive the second returned light at the timings predicted by the timing predicting section, and cause the light receiving elements to receive the first returned light at one or more timings between temporally adjacent timings among the timings predicted by the timing predicting section.

The light receiving section may include a first light receiving section having a plurality of light receiving elements that receive the first returned light and a second light receiving section having a plurality of light receiving elements that receive the second returned light.

The endoscope apparatus may further comprise a light splitting section that splits light in a wavelength region of the first returned light and light in a wavelength region of the second returned light into different optical paths, the first light receiving section may receive the first returned light resulting from the splitting by the light splitting section, and the second light receiving section may receive the second returned light resulting from the splitting by the light splitting section.

The control section may cause the light receiving elements of the second light receiving section to have multiple exposures to the second returned light at the timings predicted by the timing predicting section.

The summary clause does not necessarily describe all necessary features of the embodiments of the present invention. The present invention may also be a sub-combination of the features described above.

DESCRIPTION OF EXEMPLARY EMBODIMENTS

Hereinafter, some embodiments of the present invention will be described. The embodiments do not limit the invention according to the claims, and all the combinations of the features described in the embodiments are not necessarily essential to means provided by aspects of the invention.

Figure 1:
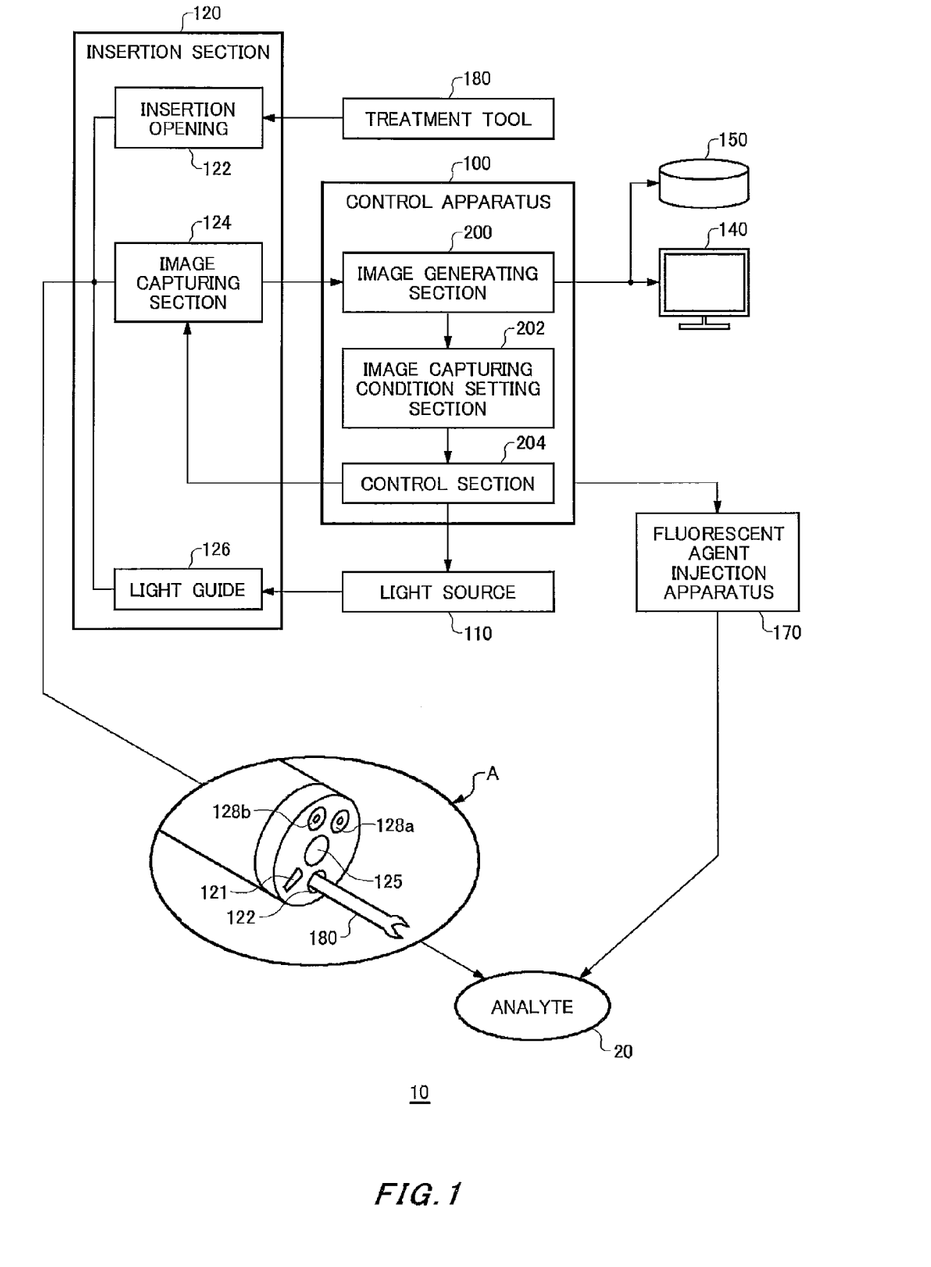
FIG. 1 shows an exemplary endoscope apparatus 10 according to an embodiment of the present invention.

FIG. 1 shows an exemplary endoscope apparatus 10 according to an embodiment of the present invention. The endoscope apparatus 10 of the present embodiment captures an image of an analyte 20, which is a living creature.

In the present embodiment, the endoscope apparatus 10 captures an image of the analyte 20 by irradiating the analyte 20 with illumination light. The endoscope apparatus 10 identifies the movement of the analyte 20 based on image content of a plurality of illumination light images. The endoscope apparatus 10 irradiates the analyte 20 with characteristic observation light at each of a plurality of timings at which the phase of the movement of the analyte 20 is a prescribed phase. The endoscope apparatus 10 generates a single characteristic observation light image by superimposing the plurality of images obtained using the characteristic observation light on each other. As a result, the endoscope apparatus 10 can generate a characteristic observation light image with higher signal strength than a case where the images are not combined. Therefore, even when the intensity of the light returned from the analyte 20 irradiated with the characteristic observation light is weak or when the analyte 20 moves, the endoscope apparatus 10 can provide an observer such as a doctor with a characteristic observation light image having a relatively high SN ratio.

The analyte 20 in the present embodiment may be an internal organ such as the stomach, intestines, or the like inside a living creature such as a person, for example. The analyte 20 may be the outside or the inside lining of an internal organ. In the present embodiment, the region serving as the image capturing target of the endoscope apparatus 10 is referred to as the analyte 20. The endoscope apparatus 10 includes an insertion section 120, a light source 110, a control apparatus 100, a fluorescent agent injection apparatus 170, a recording apparatus 150, a display apparatus 140, and a treatment tool 180. An enlarged view of the tip of the insertion section 120 is shown in section A of FIG. 1.

The insertion section 120 includes an insertion opening 122, an image capturing section 124, and a light guide 126. The tip of the insertion section 120 includes an objective lens 125 as a portion of the image capturing section 124. The tip includes an irradiating section 128a and an irradiating section 128b as a portion of the light guide 126. The irradiating section 128a and the irradiating section 128b may each include an objective lens for light emission. The irradiating section 128a and the irradiating section 128b can be referred to collectively as the irradiating section 128. The tip also includes a nozzle 121.

The insertion section 120 is inserted into an organism. A treatment tool 180, such as forceps, for treating the analyte 20 is inserted into the insertion opening 122. The insertion opening 122 guides the treatment tool 180 inserted thereto to the tip. The treatment tool 180 can have a variety of tip shapes. The nozzle 121 discharges water or air toward the analyte 20.

The light guide 126 guides the light emitted by the light source 110 to the irradiating section 128. The light guide 126 can be realized using optical fiber, for example. The irradiating section 128 emits the light guided by the light guide 126 toward the analyte 20. The image capturing section 124 receives the light returning from the analyte 20 via the objective lens 125 to capture an image of the analyte 20.

The image capturing section 124 can capture illumination light images and characteristic observation light images. The image capturing section 124 captures an illumination light image of the analyte 20 using illumination light with a relatively broad bandwidth in the visible light band. When capturing an illumination light image, the light source 110 emits substantially white light in the visible light region. The illumination light includes light in the red wavelength region, the green wavelength region, and the blue wavelength region, for example. The illumination light emitted by the light source 110 is emitted toward the analyte 20 from the irradiating section 128a via the light guide 126. The objective lens 125 receives returned light in the visible wavelength region, which is light resulting from the analyte 20 reflecting and scattering the illumination light. The image capturing section 124 captures an image via the objective lens 125 using the returned light from the analyte 20.

The characteristic observation light image may be a luminescent light image obtained using luminescent light, which is an example of the returned light from the analyte 20, for example. Fluorescent and phosphorescent light are included in the scope of the luminescent light. Furthermore, in addition to photoluminescence caused by excitation light or the like, the luminescent light can result from chemical luminescence, triboluminescence, or thermoluminescence. In the description of the present embodiment, the endoscope apparatus 10 captures a fluorescent light image as an example of the luminescent light image, using fluorescent light generated by photoluminescence.

When capturing a fluorescent light image of the analyte 20, the light source 110 generates excitation light. The excitation light generated by the light source 110 is emitted toward the analyte 20 from the irradiating section 128b, via the light guide 126. A fluorescent substance in the analyte 20 is excited by the excitation light, and therefore emits fluorescent light. The image capturing section 124 captures the fluorescent light image of the analyte 20 using the fluorescent returned light. As shown in FIG. 1, the irradiating section 128a and the irradiating section 128b may be provided at different positions on the tip, but can instead be provided at the same position on the insertion section 120 to function as an irradiating section providing both illumination light and excitation light.

The fluorescent substance is an example of a luminescent substance. The fluorescent substance may be injected to the analyte 20 from the outside. The fluorescent substance may be indo cyanine green (ICG), for example. The fluorescent agent injection apparatus 170 may inject the ICG into the blood vessels of an organism using an intravenous injection. The amount of ICG that the fluorescent agent injection apparatus 170 injects into the analyte 20 is controlled by the control apparatus 100 to maintain a substantially constant concentration of ICG in the organism. The ICG is excited by infrared rays with a wavelength of 780 nm, for example, and generates fluorescent light whose primary spectrum is in a wavelength band of 830 nm. In the present embodiment, the image capturing section 124 captures the fluorescent light image of the analyte 20 using the fluorescent light generated by the ICG.

The fluorescent substance can be a substance other than ICG. If structural components, such as cells, of the analyte 20 already contain a fluorescent substance, the image capturing section 124 may capture the fluorescent light image of the analyte 20 using the organism's own fluorescent light as the returned light.

In addition to the fluorescent light image, the characteristic observation light image may be a narrow-band light image captured by irradiating the analyte 20 with narrow-band light. The irradiating section 128b may irradiate the analyte 20 with narrow-band blue light in a blue wavelength region. The narrow-band blue light may be light in a narrower band than the light in the blue wavelength region in the illumination light. Most of the emitted narrow-band blue light is reflected and scattered by the surface of the analyte 20, to be input to the objective lens 125. As a result, a narrow-band light image in which the surface of the analyte 20 is enhanced can be obtained. In the present embodiment, the characteristic observation light image includes a fluorescent light image generated using excitation light and a narrow-band blue light image generated using the narrow-band blue light.

The image capturing section 124 can capture the image of the analyte 20 using a variety of methods other than the light returned when the analyte 20 is irradiated with the illumination light, the excitation light, and the narrow-band light. For example, the image capturing section 124 can capture an image of the analyte 20 using electromagnetic radiation, such as X-rays or y rays, or particle rays such as alpha rays. The image capturing section 124 may capture the image of the analyte 20 using sound waves, electric waves, or electromagnetic waves with a variety of wavelengths.

The control apparatus 100 includes an image generating section 200, an image capturing condition determining section 202, and a control section 204. The image generating section 200 generates an output image to be output to the outside, based on the images captured by the image capturing section 124. For example, the image generating section 200 may output the generated output image to at least one of the recording apparatus 150 and the display apparatus 140. More specifically, the image generating section 200 generates an image from the plurality of images captured by the image capturing section 124, and outputs this image to at least one of the recording apparatus 150 and the display apparatus 140. The image generating section 200 may output the output image to at least one of the recording apparatus 150 and the display apparatus 140 via a communication network such as the Internet.

The image capturing condition determining section 202 identifies relative movement of the analyte 20 with respect to the tip of the insertion section 120, based on the illumination light images generated by the image generating section 200. The image capturing condition determining section 202 determines image capturing conditions for capturing the images of the analyte 20, based on the identified movement of the analyte 20. The image capturing conditions include the type of illumination light radiated to the analyte 20, the exposure timing, the exposure duration, and the like. The control section 204 controls the image capturing section 124 and the light source 110 based on the image capturing conditions determined by the image capturing condition determining section 202.

More specifically, the image capturing condition determining section 202 identifies the movement of the analyte 20 based on the image content of a plurality of illumination light images. The image capturing condition determining section 202 determines the timings at which the fluorescent light images are to be captured to be the timings at which the phase of the movement of the analyte 20 matches a prescribed phase. The image capturing condition determining section 202 determines exposure conditions for capturing the fluorescent light image at each timing. The image generating section 200 generates a single fluorescent output image by superimposing the fluorescent light images on each other.

The display apparatus 140 displays images including the fluorescent light images and the illumination light images generated by the image generating section 200. The recording apparatus 150 records the images generated by the image generating section 200 in a non-volatile recording medium. For example, the recording apparatus 150 may store the images in a magnetic recording medium such as a hard disk or in an optical recording medium such as an optical disk.

The endoscope apparatus 10 described above can provide an observer with a fluorescent image having relatively little blur and a relatively high SN ratio. Therefore, even if the analyte 20 moves and the fluorescent light from the analyte 20 is relatively weak, the control apparatus 100 can provide the observer with a relatively clear fluorescent image.

Figure 2:
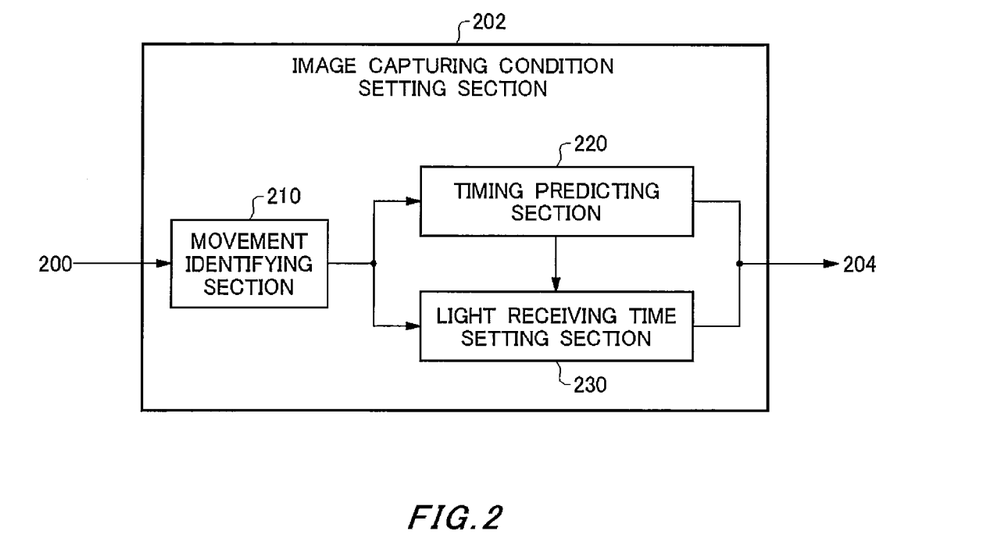
FIG. 2 shows an exemplary block configuration of the image capturing condition determining section 202.

FIG. 2 shows an exemplary block configuration of the image capturing condition determining section 202. The image capturing condition determining section 202 includes a movement identifying section 210, a timing predicting section 220, and a light receiving time setting section 230.

The irradiating section 128 of the endoscope apparatus 10 irradiates the analyte 20 with illumination light as an example of light in the first wavelength region and excitation light as an example of light in the second wavelength region, and switches between these two types of light over time. For example, the irradiating section 128a may emit the illumination light and the irradiating section 128b may emit the excitation light.

As an example, when the light source 110 includes a visible light source and an excitation light source, the control section 204 can cause the irradiating section 128a to emit the illumination light by driving the visible light source. When switching from the illumination light to the excitation light, the control section 204 can cause the excitation light from the excitation light source to be emitted from the irradiating section 128b. The illumination light source may be a discharge lamp such as a xenon lamp, a semiconductor light emitting element such as an LED, or the like. The excitation light source may be a semiconductor light emitting element such as a diode laser.

When switching from the illumination light to the excitation light, the emission of the illumination light from the irradiating section 128a can be stopped by inserting an illumination light cutoff filter that blocks the illumination light into the optical path from the visible light source while the visible light source continues to emit light. The illumination light cutoff filter may be a filter that blocks at least light in the visible light wavelength region, and may be a light-blocking filter that substantially prevents light from passing therethrough. Similarly, the switching from the excitation light to the illumination light can be achieved using an excitation light cutoff filter. The illumination light cutoff filter and the excitation light cutoff filter can be realized using filters whose light passing features can be electrically controlled, such as liquid crystal filters. The control section 204 can switch the emitted light by electrically controlling the light passing characteristics of these filters. When switching from the illumination light to the excitation light, the control section 204 may prevent the emission of the illumination light from the irradiating section 128a by stopping the driving of the LED serving as the illumination light source.

If the analyte 20 is irradiated with excitation light and narrow-band blue light as an example of the light in the second wavelength region, the light source 110 may include a narrow-band blue light source. The narrow-band blue light source can be realized using a narrow-band blue light passing filter that selectively passes light in the wavelength region of the narrow-band blue light and the visible light source. For example, the narrow-band blue light can be emitted from the irradiating section 128a by inserting the narrow-band blue light passing filter in the optical path from the visible light source. The narrow-band blue light passing filter can also be realized using a filter whose light passing characteristics are electrically controlled, such as a liquid crystal filter. The control section 204 can switch between emitting the narrow-band blue light and emitting the illumination light by electrically controlling the light passing characteristics of the narrow-band blue light passing filter. As another example, the light source 110 may include a separate narrow-band light source that generates narrow-band blue light, in addition to the visible light source. The narrow-band light source may be a semiconductor light emitting element such as an LED or diode laser. The control section 204 can cause the narrow-band blue light to be emitted from at least one of the irradiating section 128a and the irradiating section 128b by driving the narrow-band light source.

The image capturing section 124 receives the returned light from the analyte 20 irradiated with the light from the irradiating section 128. When excitation light is emitted to excite the ICG in the analyte 20, the returned light includes fluorescent light generated as a result of the ICG being excited by the excitation light. When light in a narrower band than the illumination light, e.g. narrow-band blue light, is emitted, the returned light includes light in the narrow-band blue region that results from the narrow-band blue light being reflected and scattered by the analyte 20.

The movement identifying section 210 acquires, from the image generating section 200, illumination light images captured by the image capturing section 124 receiving returned illumination light, which is the returned light from the analyte 20 irradiated with the illumination light. The returned illumination light is an example of first returned light. The movement identifying section 210 identifies the movement of the analyte 20, which is the image capturing target, based on the illumination light images.

The timing predicting section 220 predicts timings at which the phase of the movement of the analyte 20 will be a predetermined phase, based on the movement identified by the movement identifying section 210. The control section 204 of the control apparatus 100 emits excitation light, which is an example of light in the second wavelength region, from the irradiating section 128b at the timings predicted by the timing predicting section 220, and the image capturing section 124 receives fluorescent light that is the returned light from the analyte 20 irradiated with the excitation light. The fluorescent light is an example of second returned light. The image generating section 200 generates a fluorescent light image for output by superimposing on each other the fluorescent light images captured by the image capturing section 124 at the plurality of timings predicted by the timing predicting section 220.

When the characteristic observation light images are captured using narrow-band blue light, the control section 204 emits narrow-band blue light, which is an example of light in the second wavelength region, from the irradiating section 128a at the timings predicted by the timing predicting section 220, and the image capturing section 124 receives returned light in a relatively narrow wavelength region in the blue wavelength region, and this is the returned light from the analyte 20 irradiated with the narrow-band blue light. This returned light in the narrow wavelength region is an example of second returned light. The image generating section 200 generates a narrow-band blue light image for output by superimposing on each other the narrow-band blue light images captured by the image capturing section 124 at the timings predicted by the timing predicting section 220. It should be noted that the narrow-band light is not limited to narrow-band blue light. For example, narrow-band green light in the green wavelength region or narrow-band red light in the red wavelength region may be used as the narrow-band light. As another example, relatively narrow-band light in the ultra violet wavelength region or in the infrared wavelength region may be used.

The light receiving time setting section 230 sets the light receiving period during which the image capturing section 124 receives the fluorescent light at the timings predicted by the timing predicting section 220, based on the movement identified by the movement identifying section 210. Specifically, the light receiving time setting section 230 identifies the amount of movement of the analyte 20 at the timings predicted by the timing predicting section 220, based on the movement identified by the movement identifying section 210. The light receiving time setting section 230 sets the length of the light receiving period to be greater when the identified movement amount is greater. More specifically, the light receiving time setting section 230 identifies the movement amount of the analyte 20 per unit time at the timings predicted by the timing predicting section 220, based on the movement identified by the movement identifying section 210. The light receiving time setting section 230 sets the length of the light receiving period to be greater when the movement amount identified per unit time is greater.

The control section 204 causes the excitation light to be emitted from the irradiating section 128 for at least the time period determined by the light receiving time setting section 230. The control section 204 causes the image capturing section 124 to receive the fluorescent light for the period identified by the light receiving time setting section 230. When narrow-band blue light is used to capture the characteristic observation light image, the control section 204 causes narrow-band blue light to be emitted from at least one of the irradiating section 128a and the irradiating section 128b. The control section 204 causes the image capturing section 124 to receive the narrow-band blue returned light for the period determined by the light receiving time setting section 230. By controlling the image capturing conditions of the image capturing condition determining section 202, the light receiving period can be set to be shorter when the movement of the analyte 20 per unit time is greater. Therefore, the blur in the fluorescent light image and the narrow-band blue light image can be further decreased.

The function of the control apparatus 100 may be implemented by a computer. Specifically, by installing a program implementing the function of the control apparatus 100 in a computer, the computer may function as the image generating section 200, the components of the image capturing condition determining section 202, and the control section 204. This program may be stored in a computer readable recording medium such as a CD-ROM or hard disk, and may be provided to the computer by having the computer read the program from the recording medium. The program may be provided to the computer via a network.

Figure 3:
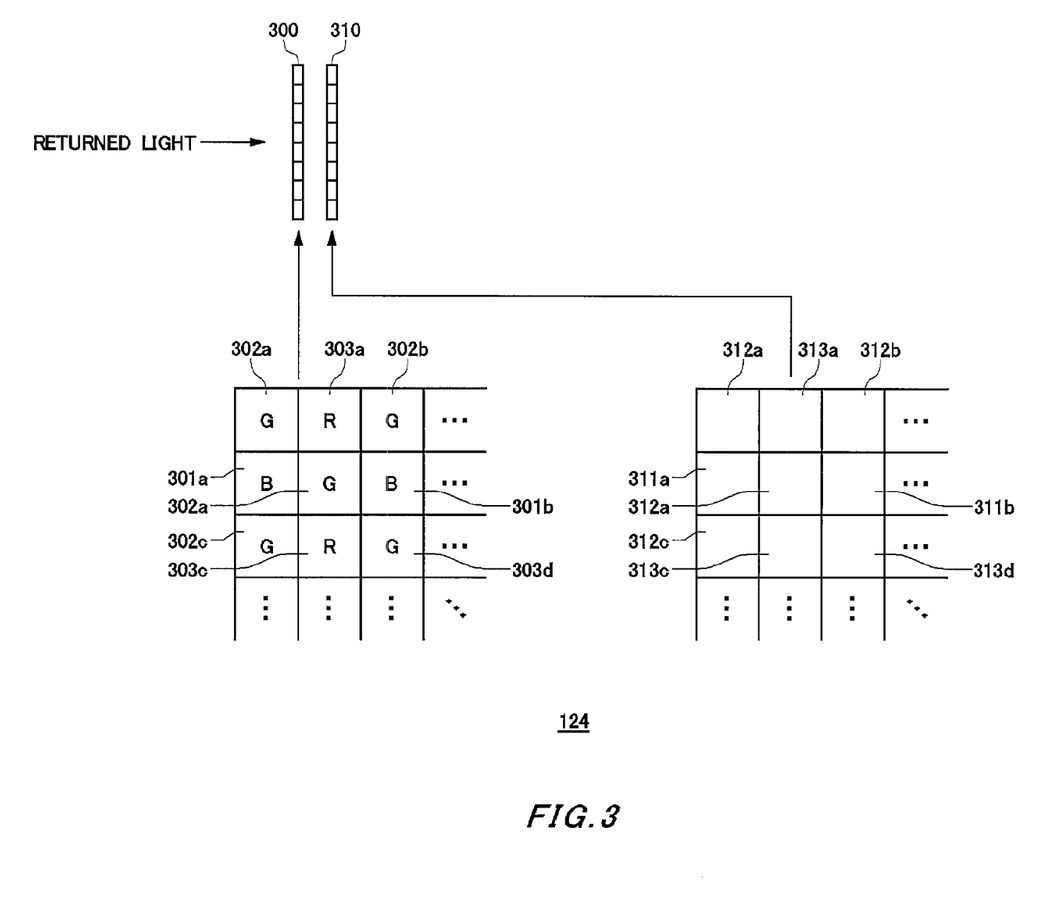
FIG. 3 is a schematic view of an exemplary configuration of a light receiving unit of the image capturing section 124.

FIG. 3 is a schematic view of an exemplary configuration of a light receiving unit of the image capturing section 124. The light receiving unit includes a wavelength filter section 300 and a light receiving section 310. The returned light from the analyte 20 passes through the objective lens 125 and the wavelength filter section 300 to be received by the light receiving section 310.

The wavelength filter section 300 includes a plurality of blue light passing filters 301 that selectively pass light in the blue wavelength region, a plurality of green light passing filters 302 that selectively pass light in the green wavelength region, and a plurality of red light passing filters 303 that pass at least light in the red wavelength region. In FIG. 3, the blue light passing filters 301a and 301b, green light passing filters 302a to 302d, and red light passing filters 303a and 303c are shown. The blue light passing filter 301a, two green light passing filters 302a, and a red light passing filter 303a are arranged in a matrix to form one wavelength filter unit. The wavelength filter section 300 may have a wavelength filter array in which a plurality of such wavelength filter units are arranged in a matrix, in the same manner as the light passing filters within a wavelength filter unit.

The light receiving section 310 may be formed by arranging a plurality of light receiving elements at positions to selectively receive light passed by the blue light passing filters 301, the green light passing filters 302, and the red light passing filters 303. Specifically, the light receiving section 310 may have a light receiving element array in which a plurality of blue light receiving sections 311 that selectively receive light in the blue wavelength region, a plurality of green light receiving sections 312 that selectively receive light in the green wavelength region, and a plurality of red light receiving sections 313 that receive at least light in the red wavelength region are arranged two-dimensionally.

More specifically, a blue light receiving section 311a receives light passed by a blue light passing filter 301a, a green light receiving section 312a receives light passed by a green light passing filter 302a, and a red light receiving section 313a receives light passed by a red light passing filter 303a. Each light receiving element may be an image capturing element, such as a CCD or a CMOS. When illumination light is emitted from the irradiating section 128a, the image capturing section 124 can capture an illumination light image of visible light using the blue light receiving sections 311, the green light receiving sections 312, and the red light receiving sections 313.

Here, in addition to light in the red wavelength region, the red light passing filters 303 can also pass the wavelength region of the fluorescent light emitted by the ICG. In other words, the red light passing filters 303 selectively pass light in the red wavelength region and in the fluorescent light wavelength region. When excitation light is emitted from the irradiating section 128a, the fluorescent light emitted by the ICG passes through the red light passing filters 303 to be received by the red light receiving sections 313. Accordingly, the image capturing section 124 can capture the fluorescent light images using the red light receiving sections 313. It is preferable that at least the red light passing filters 303 have light passing frequencies to substantially block light in the wavelength region of the excitation light, such that at least the red light receiving sections 313 receiving the fluorescent light do not receive light in the wavelength region of the excitation light. An excitation light cutoff filter than blocks light in the wavelength region of the excitation light may be provided over the entire surface functioning as the wavelength filter section 300.

If narrow-band blue light images are being captured as the characteristic observation light images simultaneously with the fluorescent light images, the narrow-band blue returned light is received by the blue light receiving sections 311. The image capturing section 124 can capture the narrow-band blue light images using the blue light receiving sections 311.

Figure 4:
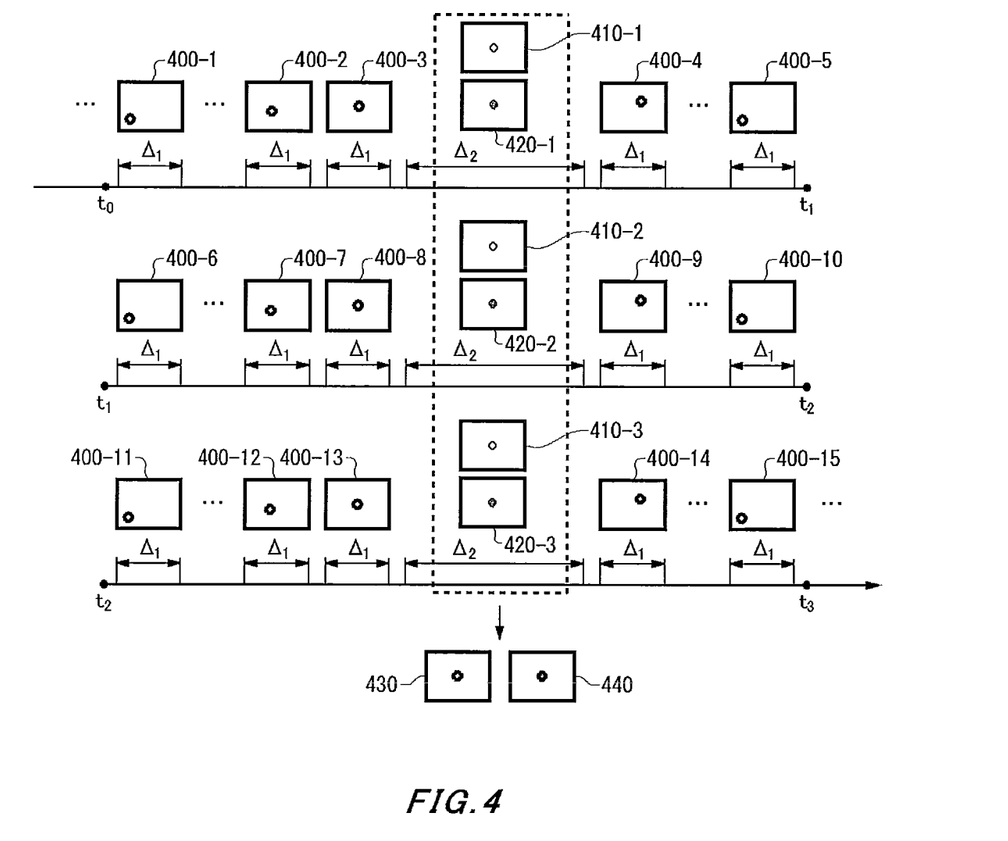
FIG. 4 shows exemplary timings of capturing the illumination light images and the characteristic observation light images.

FIG. 4 shows exemplary timings of capturing the illumination light images and the characteristic observation light images. The illumination light images 400-1 to 400-5 are captured within one cycle of the movement of the analyte 20. The illumination light images 400-6 to 400-10 are captured in the next cycle of the movement of the analyte 20, and the illumination light images 400-11 to 400-15 are captured in the cycle after that. The illumination light images 400 are captured by exposing the light receiving section 310 to the illumination light over a predetermined time period Δ1. By repeating this exposure over a predetermined image capturing period, a series of illumination light images 400 are captured. The image capturing section 124 can capture the illumination light images 400 using the blue light receiving sections 311, the green light receiving sections 312, and the red light receiving sections 313.

The movement identifying section 210 detects the movement of the analyte 20 based on the illumination light images 400-1 to 400-3. For example, the movement identifying section 210 may identify the position and shape of a specified object captured in each of the illumination light images 400-1 to 400-3, using image processing such as object extraction. In this way, the movement identifying section 210 detect the movement of the analyte 20 in real time. The movement identifying section 210 may set the target of the object extraction to be a distinct object from among a plurality of objects extracted from the illumination light images 400. This distinct object may be the object that is farthest from other objects in an image feature value coordinate system. The object that is farthest from other objects in the image feature value coordinate system may refer to the object that is farthest from a closest object in the image feature value coordinate system The movement identifying section 210 identifies positional change over time of the object, based on the time at which the illumination light images 400-1 to 400-3 were captured and the position of the object in these illumination light images 400. The movement identifying section 210 also identifies the shape change over time of the object, based on the time at which the illumination light images 400-1 to 400-3 were captured and the position of the object in these illumination light images 400.

The timing predicting section 220 predicts a period during which the position and shape of the object remain substantially constant. For example, the timing predicting section 220 may identify timings at which the displacement of the object per unit time is less than a predetermined threshold value and the deformation of the object per unit time is less than a predetermined threshold value. The index for the change in shape can be the size of the object. In the example of FIG. 4, the position and shape of the object are predicted to be substantially constant for longer than a predetermined period after the illumination light image 400-3 is captured. For example, until a timing before the illumination light image 400-4 is captured, the position and the shape of the object are predicted to be substantially constant.

After the illumination light image 400-3 is captured, the control section 204 causes excitation light and narrow-band blue light to be emitted from the irradiating section 128 for at least a time period Δ2. As a result, the image capturing section 124 captures the fluorescent light image 410-1 and the narrow-band blue light image 420-1. More specifically, the image capturing section 124 can capture the fluorescent light image 410-1 using the red light receiving sections 313 and capture the narrow-band blue light image 420-1 using the blue light receiving sections 311.

Here, the time period Δ2 is longer than the time period Δ1. In other words, the control section 204 causes the light receiving section to receive fluorescent light and narrow-band blue returned light at each of the timings predicted by the timing predicting section 220, over a time period that is longer than the time period Δ1 during which the light receiving section 310 receives illumination returned light to capture one illumination light image 400. As a result, the acquired fluorescent light image 410-1 and narrow-band blue light image 420-1 are clearer than images acquired when the exposure time is the same as the exposure time for the illumination light image.

After the fluorescent light image 410-1 and the fluorescent light image 420-2 are captured, the control section 204 captures the illumination light images 400-4 and 400-5. More specifically, the control section 204 captures the illumination light images 400-4 and 400-5 by exposing the light receiving section 310 to the illumination light during prescribed image capturing periods for the predetermined time period Δ1.

After the time t1, the movement of the analyte 20 in the period from t1 to t2 and in the period from t2 to t3 is substantially the same as the movement in the period from t0 to t1. In this case, the control section 204 switches between image capturing with the illumination light and image capturing with the characteristic observation light at the same timings that the illumination light images 400-1 to 400-5, the fluorescent light image 410-1, and the narrow-band blue light image 420-1 are captured at. As a result, the image capturing section 124 captures the illumination light images 400-1 to 400-15, the fluorescent light images 410-2 and 410-3, and the narrow-band blue light images 420-2 and 420-3.

In this way, the image capturing section 124 captures a plurality of images using the illumination light while capturing images using the characteristic observation light. In other words, the control section 204 causes the light receiving section 310 to receive visible returned light at one or more timings between temporally adjacent timings among the timings of the image capturing using the characteristic observation light. The image generating section 200 generates the illumination light image based on each of the one or more timings, based on the visible returned light received by the light receiving section 310.

As described in relation to FIG. 3, the red light receiving sections 313 can receive fluorescent light and light in the red wavelength region, and therefore the red light receiving sections 313 used for capturing the illumination light images can also be used to capture the fluorescent light images. In other words, the control section 204 causes the red light receiving sections 313 of the light receiving section 310 to receive fluorescent light at the timings of the image capturing using the characteristic observation light. The control section 204 also causes the red light receiving sections 313 to receive the illumination returned light at one or more timings between temporally adjacent timings among the timings of the image capturing using the characteristic observation light.

The image generating section 200 generates the fluorescent light image 430 for output by superimposing corresponding pixels of the fluorescent light images 410-1, 410-2, and 410-3 on each other. The image generating section 200 generates the narrow-band blue light image 440 for output by superimposing corresponding pixels of the narrow-band blue light images 420-1, 420-2, and 420-3 on each other. In this way, the image generating section 200 generates the fluorescent light image 430 by adding together signals indicating the amount of fluorescent light received by the light receiving section 310 at each of the timings predicted by the timing predicting section 220. The image generating section 200 may apply a binning process to the fluorescent light images 430.

The image generating section 200 may perform the superimposition to generate the fluorescent light image 430 after applying the binning process as image processing to each of the fluorescent light images 410-1, 410-2, and 410-3. As another example, the image capturing section 124 may perform the binning process on the image capture signals of the fluorescent light images 410-1, 410-2, and 410-3, and output the resulting signals to the image generating section 200. In other words, when reading the image corresponding to the fluorescent light image 410-1, the image capturing section 124 may perform binning reading and output the result to the image generating section 200 as the image capture signal of the fluorescent light image 410-1. The image generating section 200 generates the fluorescent light image 410-1 based on this image capture signal. The fluorescent light images 410-2 and 410-3 may be generated from the image capture signals obtained via binning reading in the same manner. The image generating section 200 may then generate the fluorescent light image 430 by superimposing the fluorescent light images 410-1, 410-2, and 410-3 obtained form the binning reading.

The image generating section 200 generates the narrow-band blue light image 440 by adding together the signals indicating the amount of narrow-band blue light received by the light receiving section 310 at each of the timings predicted by the timing predicting section 220. The process for generating the narrow-band blue light image 440 is the same as the process for generating the fluorescent light image 430, and therefore further description is omitted. The image generating section 200 outputs the generated fluorescent light image 430 and narrow-band blue light image 440 to the outside, e.g. to the display apparatus 140 and the recording apparatus 150.

In this way, the endoscope apparatus 10 can acquire a characteristic observation light image with relatively little blur by capturing characteristic observation light images at timings at which the movement of the analyte 20 has substantially the same phase. Furthermore, by superimposing the characteristic observation light images on each other, the endoscope apparatus 10 can acquire a characteristic observation light image with a high SN ratio by decreasing the random noise, for example.

In the example of FIG. 4, the image capturing section 124 captures characteristic observation light images at a single movement phase in each cycle of the movement of the analyte 20. However, the endoscope apparatus 10 can capture characteristic observation light images at each of a plurality of different phases. For example, the image capturing section 124 may capture characteristic observation light images at each of a plurality of different movement phases in each cycle of the movement of the analyte 20. The image generating section 200 may then generate one characteristic observation light image to be output for each movement phase, by superimposing the characteristic observation light images at each movement phase on each other. The display apparatus 140 may switch to display the characteristic observation light image corresponding to the current movement phase, in synchronization with the display of the illumination light image.

Figure 5:
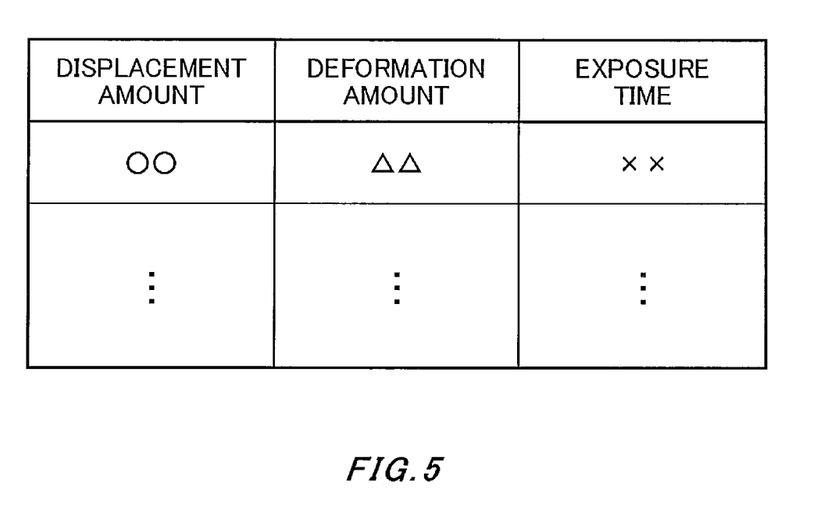
FIG. 5 shows an exemplary table of information stored by the light receiving time setting section 230.

FIG. 5 shows an exemplary table of information stored by the light receiving time setting section 230. The light receiving time setting section 230 stores allowable exposure times in association with displacement amounts and deformation amounts. The displacement amount may indicate the change amount per unit time of the position of the object in the image, for example. The deformation amount may refer to the change amount per unit time of the size of the object in the image, for example. The exposure time is the maximum value for the time period over which the light receiving section 310 can be exposed when capturing a single characteristic observation light image to be used in the superimposition. The light receiving time setting section 230 references this table to determined the exposure time $\Delta 2$ when capturing one characteristic observation light image.

More specifically, the movement identifying section 210 extracts the distinct object from each of the illumination light images 400, and identifies the size of the distinct object and the position of the center of the distinct object in the plane of the image. The light receiving time setting section 230 calculates the change amount of the center position of the distinct object per unit time, based on the center position of the distinct object in each illumination light image 400. The light receiving time setting section 230 calculates the change in size of the distinct object per unit time, based on the size of the distinct object in each illumination light image 400.

The light receiving time setting section 230 references the table to select the exposure time stored in association with the displacement amount closest to the calculated change amount of the displacement. If different deformation amounts are associated with the displacement amount closest to the calculated change amount of the displacement, the light receiving time setting section 230 selects the exposure time stored in association with the deformation amount closest to the calculated change amount of the size. The light receiving time setting section 230 determines a value no greater than the selected exposure time to be used as the time period $\Delta 2$ of the exposure when capturing a characteristic observation light image. As a result, a suitable maximum value can be determined for the exposure time to restrict image blurring, according to the displacement amount or to the displacement amount and deformation amount.

Every time a characteristic observation light image is captured, the image generating section 200 stores the characteristic observation light image is a temporary storage memory. Furthermore, the image generating section 200 adds the exposure time used for the characteristic observation light image, as determined by the light receiving time setting section 230, to an exposure time counter that has an initial value of 0. When the exposure time counter exceeds a predetermined value, the image generating section 200 may superimpose the characteristic observation light images stored in the memory onto each other to generate one characteristic observation light image for output and initialize the exposure time counter. As a result, when the analyte 20 moves little and a longer exposure time is used for capturing the characteristic observation light image, the image generating section 200 can generate the one characteristic observation light image for output from a lower number of characteristic observation light images. Therefore, when the analyte 20 moves little, the characteristic observation light image for output can be updated more frequently.

In the above description, the fluorescent light is received by the red light receiving sections 313. Instead, the wavelength filter section 300 may include fluorescent light receiving elements that selectively receive fluorescent light and are separate from the red light receiving elements. For example, a fluorescent light passing filter may be provided in place of one of the two green light passing filters 302a shown in FIG. 3. In this case, the light receiving element at the corresponding position can function as a fluorescent light receiving element that selectively receives fluorescent light.

Figure 6:
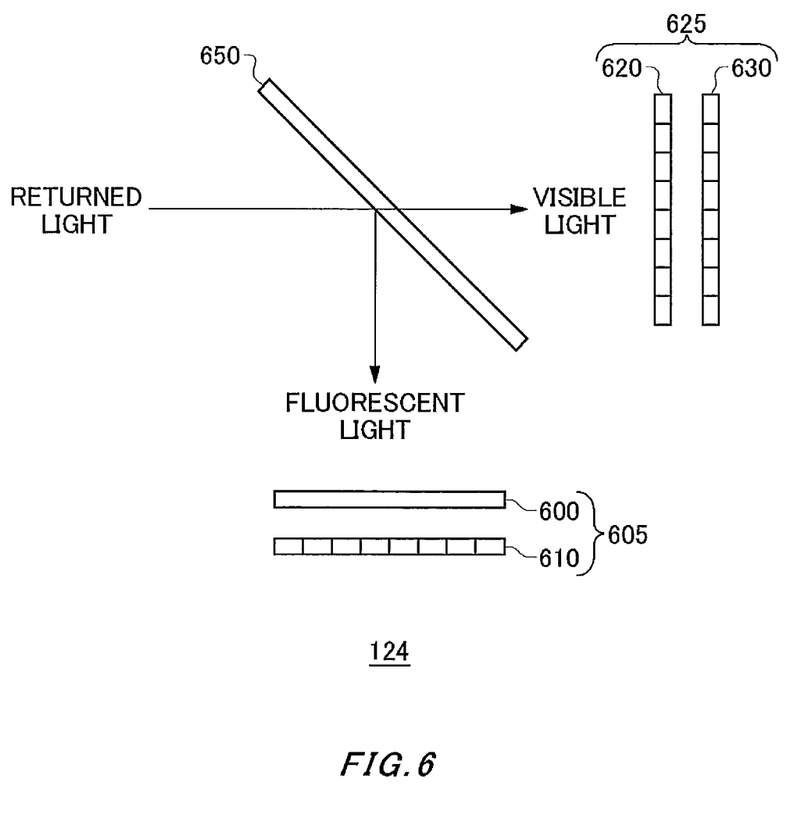
FIG. 6 shows another exemplary configuration of a light receiving unit of the image capturing section 124.

FIG. 6 shows another exemplary configuration of a light receiving unit of the image capturing section 124. The image capturing section 124 of the present embodiment includes a light receiving unit that receives fluorescent light and a light receiving unit that captures images using illumination returned light, and these two light receiving units are distanced from each other. Specifically, the image capturing section 124 includes a first light receiving unit 625, which has a first wavelength filter section 620 and a first light receiving section 630, and a second light receiving unit 605, which has a second wavelength filter section 600 and a second light receiving section 610. The image capturing section 124 includes a light splitting section 650 in addition to the objective lens 125, as the image capturing optical system.

The light splitting section 650 splits, into different optical paths, the visible light and the fluorescent light included in the returned light from the analyte 20 passed through the objective lens 125. The light splitting section 650 guides the resulting fluorescent light to the second light receiving unit 605 and guides the resulting visible light to the first light receiving unit 625. The light splitting section 650 may be realized by a dichromatic mirror or a dichromatic prism. The first light receiving section 630 receives the illumination returned light from the splitting. The second light receiving section 610 receives the fluorescent light from the splitting.

The first wavelength filter section 620 may have a visible light wavelength filter array in which blue light passing filters, green light passing filters, and red light passing filters are arranged in the same manner as in the wavelength filter section 300. In the present embodiment, red light passing filters of the first wavelength filter section 620 need not pass light in the fluorescent light wavelength region as long as they pass light in the red wavelength region. The first light receiving section 630 may have a light receiving element array in which light receiving elements are arranged in the same manner as in the light receiving section 310. The light receiving elements of the first light receiving section 630 can receive the illumination returned light. The illumination light images can be captured by the first light receiving section 630 receiving the illumination returned light resulting from the splitting by the light splitting section 650.

The second wavelength filter section 600 has light passing characteristics to pass at least fluorescent light. The second wavelength filter section 600 may have light passing characteristics to block at least excitation light. The second wavelength filter section 600 may have light passing characteristics to block light in the visible light wavelength spectrum. If the second light receiving unit 605 substantially receives only light in the fluorescent light wavelength region as a result of the returned light being split by the light splitting section 650, the second wavelength filter section 600 need not be provided. If the second light receiving section 610 receives fluorescent light in a plurality of different wavelength regions to capture fluorescent light images in different wavelength regions, wavelength filters that pass light in different wavelength regions may be provided in a two-dimensional arrangement.

The second light receiving section 610 receives fluorescent light passed through the second wavelength filter section 600. The second light receiving section 610 may have a light receiving element array in which light receiving elements that can receive fluorescent light are arranged in the same manner as in the light receiving section 310. With the light receiving units of the present embodiment, the illumination light images and fluorescent light images can be captured by different light receiving units. Therefore, it is easy to capture a single fluorescent light image for output by performing multiple exposures of the second light receiving section 610 to the fluorescent light. Furthermore, the illumination light images and the fluorescent light images can be captured at the same time.

Figure 7:
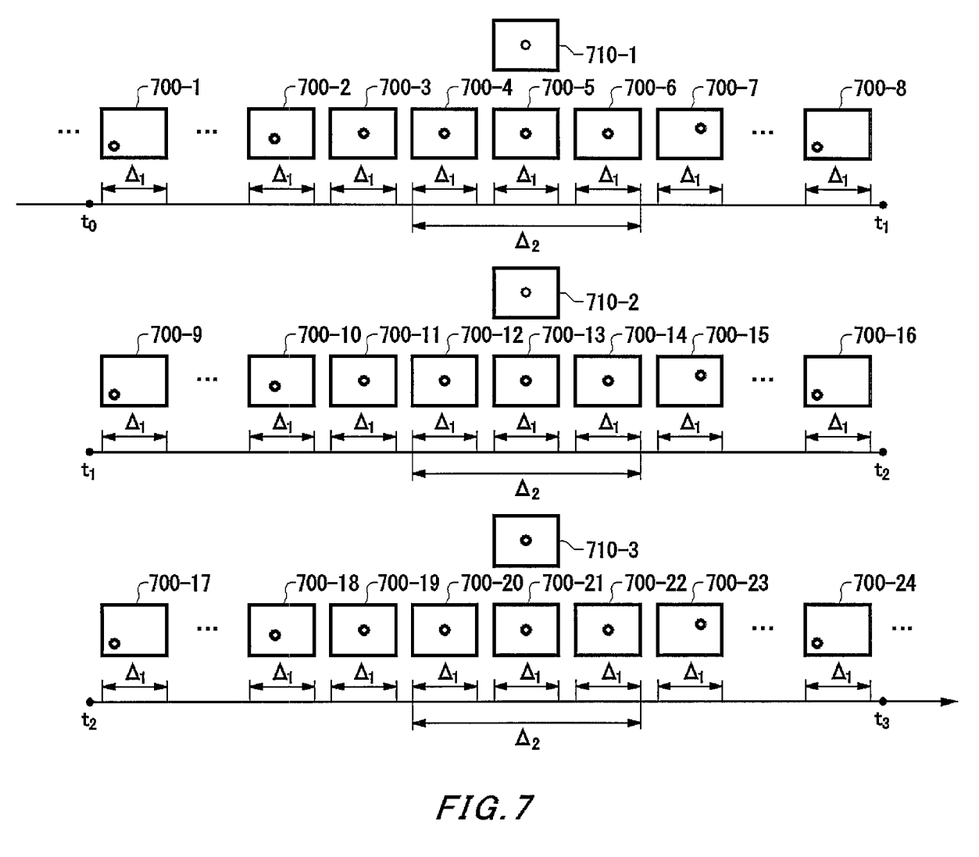
FIG. 7 shows exemplary image capturing timings by the first light receiving unit 625 and the second light receiving unit 605.

FIG. 7 shows exemplary image capturing timings by the first light receiving unit 625 and the second light receiving unit 605. In FIG. 7, the image capturing section 124 captures a plurality of illumination light images 700 and a fluorescent light image 710-3 for output.

The illumination light images 700-1 to 700-8 are captured in one cycle of the analyte 20 movement. The illumination light images 700-9 to 700-16 are captured in the next cycle of the analyte 20 movement, and the illumination light images 700-17 to 700-24 are captured in the cycle after that. The illumination light images 700 are captured by exposing the light receiving section 310 to the illumination light during the predetermined time period Δ1. By repeating this exposure over a predetermined image capturing period, a series of illumination light images 700 are captured.

The movement identifying section 210 detects the movement of the analyte 20 based on the illumination light images 700-1 to 700-3. The process by which the movement identifying section 210 identifies the analyte 20 movement is the same as the process described in relation to FIGS. 4 and 5 by which the movement identifying section 210 identifies the movement of the analyte 20 from the illumination light images 400, and therefore further description is omitted. In the example of FIG. 7, it is predicted that the position and size of the object will remain substantially constant for longer than the predetermined time period after the illumination light image 700-3 is captured. For example, the position and size of the object are predicted to remain constant for longer than double the image capturing period of an illumination light image.

After the illumination light image 700-3 is captured, the control section 204 causes excitation light to be emitted from the irradiating section 128*b* for at least a time period Δ2 and exposes the second light receiving section 610. The control section 204 continues to expose the first light receiving section 630 to the illumination light emitted from the irradiating section 128*a* while the excitation light is also being emitted. Due to the splitting by the light splitting section 650, the second light receiving section 610 is exposed to the fluorescent light in the returned light from the analyte 20 and the first light receiving section 630 is exposed to the illumination light in the returned light from the analyte 20.

Here, the time period Δ2 is longer than the time period Δ1. For example, the time period Δ2 may be an integer multiple, greater than 1, of the time period Δ1. The first light receiving section 630 may be exposed a plurality of times within the period in which the second light receiving section 610 is exposed to the fluorescent light. In the example of FIG. 7, three illumination light images 700-4 to 700-6 are obtained by exposing the first light receiving section 630 three times. In this way, the control section 204 causes the second light receiving section 610 to receive fluorescent light over a period during which the first light receiving section 630 performs a plurality of image captures using the illumination light.

After the fluorescent light image 710-6 is captured, the control section 204 captures the illumination light images 700-7 and 700-8. More specifically, the control section 204 captures the illumination light images 700-7 and 700-8 by exposing the first light receiving section 630 to the illumination light for predetermined image capturing periods over the predetermined time period Δ1. In this way, the control section 204 captures the illumination light images 700 at prescribed image capturing periods in the period from the time t0 to t1.

Here, after the second light receiving section 610 is exposed to the fluorescent light, the control section 204 does not read the received light signals from the light receiving elements of the second light receiving section 610, and so the light receiving elements of the second light receiving section 610 hold the received light signals. More specifically, the charge generated by the exposure of the light receiving elements of the second light receiving section 610 is held by each light receiving element.

After the time t1, the movement of the analyte 20 in the period from t1 to t2 and in the period from t2 to t3 is substantially the same as the movement in the period from t0 to t1. In this case, image capturing with the illumination light is performed at the same timings that the illumination light images 700-1 to 700-8 were captured at. As a result, the image capturing section 124 captures the illumination light images 700-9 to 700-24. The illumination light images 700 captured by the image capturing section 124 are output to the outside, e.g. to the display apparatus 140 and the recording apparatus 150.

During the time period from t1 to t3, the control section 204 performs multiple exposures of the second light receiving section 610 at second timings corresponding to fluorescent light exposure timings in the time period from t0 to t1 while the light receiving elements of the second light receiving section 610 continue to hold the received light signals. In this way, the control section 204 causes the light receiving elements of the second light receiving section 610 to receive multiple exposures to the fluorescent light at a plurality of timings. Therefore, as shown generally in the fluorescent light images 710-1 to 710-3, the signal amount gradually increases each time an exposure is performed. After the second light receiving section 610 is exposed to the fluorescent light three times, the control section 204 reads the received light signals from the light receiving elements of the second light receiving section 610 and causes the image generating section 200 to generate the fluorescent light image 710-3 for output. The image capturing section 124 may perform the binning process on the image capture signal of the fluorescent light image 710-3, and output the resulting signal to the image generating section 200. In other words, the image capturing section 124 may perform binning reading when reading the fluorescent light image 710-3.

Since the fluorescent light image for output is obtained by multiple exposures of the second light receiving section 610 to the fluorescent light, a longer exposure time can be effectively ensured. Therefore, a fluorescent light image for output with a high SN ratio can be obtained. Furthermore, in the same manner as the image capturing flow described in relation to FIG. 4, a fluorescent light image for output with little image blur can be obtained by performing exposure at timings when the movement of the analyte 20 is at substantially the same phase.

A plurality of fluorescent light images may be generated without performing multiple exposures, by reading the received light signals from the light receiving elements of the second light receiving section 610 for each fluorescent light exposure period and using the superimposition process described in relation to FIG. 4 or the like. The image generating section 200 may generate the fluorescent light image for output by superimposing a plurality of fluorescent light images captured by the second light receiving section 610 receiving light. In this way, the image generating section 200 can generate the fluorescent light image for output with a relatively high SN ratio by performing multiple exposures of the second light receiving section 610 or by superimposing fluorescent light images captured at different timings on each other. In other words, the image generating section 200 can generate a fluorescent light image of the analyte 20 based on the fluorescent light received by the light receiving section at the plurality of timings predicted by the timing predicting section 220.

The time period Δ2 of the fluorescent light image capturing may be set by the light receiving time setting section 230 in the same manner as described in relation to FIGS. 4 and 5. The movement identifying section 210 may detect the movement of the analyte 20 based on the content of illumination light images 700 captured during the fluorescent light image capturing, such as the illumination light images 700-4 to 700-6. The control section 204 may expose the second light receiving section 610 to the fluorescent light on the condition that the position and/or size of the object identified by the movement identifying section 210 is within a predetermined range. In other words, when the position and/or size of the object is outside of the predetermined range, the control section 204 may stop the exposure of the second light receiving section 610 to the fluorescent light, for example, to stop the image capturing of the fluorescent light images by the second light receiving section 610. By detecting the movement of the analyte 20 from illumination light images 700 including illumination light images 700 captured during the fluorescent light image capturing, the fluorescent light exposure time can be made as long as possible. Furthermore, even if the analyte 20 moves in an unexpected manner, significant blur in the fluorescent light image for output can be prevented in advance by the control section 204 stopping the exposure of the second light receiving section 610 and/or stopping the emission of excitation light from the irradiating section 128b.

If the total amount of fluorescent light exceeds a predetermined value, the control section 204 may stop the multiple exposure of the second light receiving section 610. More specifically, the control section 204 gradually adds the duration of the fluorescent light exposure time to the exposure time counter having an initial value of 0. When the exposure time counter exceeds a predetermined value, the control section 204 reads the received light signals from the light receiving elements of the second light receiving section 610 and causes the image generating section 200 to generate the fluorescent light image for output. The control section 204 then initializes the exposure time counter. As a result, when the analyte 20 moves little and a longer exposure time is used for capturing the fluorescent light images, the image generating section 200 can generate one fluorescent light image for output from a shorter exposure time. Therefore, when the analyte 20 moves little, the fluorescent light image for output can be updated more frequently.

While the embodiments of the present invention have been described, the technical scope of the invention is not limited to the above described embodiments. It is apparent to persons skilled in the art that various alterations and improvements can be added to the above-described embodiments. It is also apparent from the scope of the claims that the embodiments added with such alterations or improvements can be included in the technical scope of the invention.

The operations, procedures, steps, and stages of each process performed by an apparatus, system, program, and method shown in the claims, embodiments, or diagrams can be performed in any order as long as the order is not indicated by "prior to," "before," or the like and as long as the output from a previous process is not used in a later process. Even if the process flow is described using phrases such as "first" or "next" in the claims, embodiments, or diagrams, it does not necessarily mean that the process must be performed in this order.

What is claimed is:

1. An endoscope apparatus comprising:
   an irradiating section that switches over time between irradiating a target with light in a first wavelength region and light in a second wavelength region;
   a light receiving section that receives returned light from the target irradiated with the light from the irradiating section;
   a movement identifying section that identifies movement of the target, based on a first image of the target captured as a result of the light receiving section receiving first returned light, which is returned light from the target irradiated by the light in the first wavelength region;
   a timing predicting section that predicts a plurality of timings at which a phase of the movement of the target is a predetermined phase, based on the movement identified by the movement identifying section;
   a control section that causes the irradiating section to emit the light in the second wavelength region at the timings predicted by the timing predicting section and causes the light receiving section to receive second returned light, which is returned light from the target irradiated by the light in the second wavelength region; and
   an image generating section that generates a second image of the target based on the second returned light received by the light receiving section at the timings predicted by the timing predicting section.

2. The endoscope apparatus according to claim 1, wherein the control section causes the light receiving section to receive the first returned light at one or more timings between temporally adjacent timings among the timings predicted by the timing predicting section, and the image generating section generates the first image at each of the one or more timings, based on the first returned light received by the light receiving section.

3. The endoscope apparatus according to claim 1, wherein the control section causes the light receiving section to receive the second returned light at each of the timings predicted by the timing predicting section, over a period longer than the period during which the light receiving section receives the first returned light to capture one of the first images.

4. The endoscope apparatus according to claim 1, further comprising a light receiving time setting section that sets length of a light receiving period during which the light receiving section receives the second returned light at the timings predicted by the timing predicting section, based on the movement identified by the movement identifying section, wherein
 the control section causes the light receiving section to receive the second returned light for the period length set by the light receiving time setting section.

5. The endoscope apparatus according to claim 4, wherein the light receiving time setting section identifies movement amount of the target at the timings predicted by the timing predicting section, based on the movement identified by the movement identifying section, and sets the light receiving period to be longer when the identified movement amount is larger.

6. The endoscope apparatus according to claim 1, wherein the light in the second wavelength region is excitation light that excites a luminescent substance in the target, and the second returned light is luminescent light generated by the luminescent substance being excited by the excitation light.

7. The endoscope apparatus according to claim 1, wherein the light in the second wavelength region is light in a narrower band than the light in the first wavelength region.

8. The endoscope apparatus according to claim 1, wherein the light in the first wavelength region is light in a visible wavelength region.

9. The endoscope apparatus according to claim 1, wherein the image generating section generates the second image by adding together signals indicating an amount of the second returned light received by the light receiving section at each of the timings predicted by the timing predicting section.

10. The endoscope apparatus according to claim 1, wherein the control section causes light receiving elements of the light receiving section to receive the second returned light at the timings predicted by the timing predicting section, and causes the light receiving elements to receive the first returned light at one or more timings between temporally adjacent timings among the timings predicted by the timing predicting section.

11. The endoscope apparatus according to claim 1, wherein the light receiving section includes:
 a first light receiving section having a plurality of light receiving elements that receive the first returned light; and
 a second light receiving section having a plurality of light receiving elements that receive the second returned light.

12. The endoscope apparatus according to claim 11, further comprising a light splitting section that splits light in a wavelength region of the first returned light and light in a wavelength region of the second returned light into different optical paths, wherein
 the first light receiving section receives the first returned light resulting from the splitting by the light splitting section, and
 the second light receiving section receives the second returned light resulting from the splitting by the light splitting section.

13. The endoscope apparatus according to claim 11, wherein
 the control section causes the light receiving elements of the second light receiving section to have multiple exposures to the second returned light at the timings predicted by the timing predicting section.

14. A method for controlling an endoscope apparatus including an irradiating section that emits light and a light receiving section that receives returned light from a target irradiated with the light from the irradiating section, the method comprising:
 identifying movement of the target, based on a first image of the target captured as a result of the light receiving section receiving first returned light, which is returned light from the target irradiated by light in a first wavelength region;
 predicting a plurality of timings at which a phase of the movement of the target is a predetermined phase, based on the identified movement;
 causing the irradiating section to switch from emitting the light in the first wavelength region to emitting the light in the second wavelength region at the predicted timings, and causing the light receiving section to receive second returned light, which is returned light from the target irradiated by light in a second wavelength region; and
 generating a second image of the target based on the second returned light received by the light receiving section at the predicted timings.

15. A non-transitory computer readable medium storing thereon a program for use by an endoscope apparatus including an irradiating section that emits light and a light receiving section that receives returned light from a target irradiated with the light from the irradiating section, the program causing a computer to function as:
 an irradiation control section that causes the irradiating section to switch over time between irradiating the target with light in a first wavelength region and light in a second wavelength region
 a movement identifying section that identifies movement of the target, based on a first image of the target captured as a result of the light receiving section receiving first returned light, which is returned light from the target irradiated by the light in the first wavelength region;
 a timing predicting section that predicts a plurality of timings at which a phase of the movement of the target is a predetermined phase, based on the movement identified by the movement identifying section;
 a control section that causes the irradiation control section to emit the light in the second wavelength region at the timings predicted by the timing predicting section and causes the light receiving section to receive second returned light, which is returned light from the target irradiated by the light in the second wavelength region; and
 an image generating section that generates a second image of the target based on the second returned light received by the light receiving section at the timings predicted by the timing predicting section.

* * * * *